United States Patent [19]

Stein et al.

[11] Patent Number: 4,565,736
[45] Date of Patent: Jan. 21, 1986

[54] FIBROUS SURGICAL COMPRESS WITH COVER LAYER AUTOGENOUSLY BONDED TO ABSORPTION LAYER

[75] Inventors: Karl H. Stein, Hemsbach; Manfred Krull, Heiligkreuzsteinach, both of Fed. Rep. of Germany

[73] Assignee: Firma Carl Freudenberg, Weinheim/Bergstr, Fed. Rep. of Germany

[21] Appl. No.: 477,073

[22] Filed: Mar. 21, 1983

Related U.S. Application Data

[63] Continuation of Ser. No. 301,101, Sep. 17, 1981, abandoned.

[30] Foreign Application Priority Data

Sep. 30, 1980 [DE] Fed. Rep. of Germany ....... 3036814

[51] Int. Cl.⁴ ............................................. B32B 27/00
[52] U.S. Cl. ................................... 428/286; 156/62.8; 156/176; 156/244.23; 428/288; 428/296; 428/298; 428/300; 428/301; 428/302
[58] Field of Search ............... 428/286, 288, 296, 298, 428/300, 301, 302; 156/62.8, 176, 244.23

[56] References Cited

U.S. PATENT DOCUMENTS 3,902,484 9/1975 Winters .......................... 128/132 D
3,978,855 9/1976 McRae ........................... 128/132 D

FOREIGN PATENT DOCUMENTS 7703897 6/1977 Fed. Rep. of Germany .

Primary Examiner—Marion C. McCamish
Attorney, Agent, or Firm—Kenyon & Kenyon

[57] ABSTRACT

A surgical compress is described which is made of an absorptive layer and a wound covering layer, the covering layer spun or otherwise made of nonwoven hydrophobic fibers so that absorption of wound secretions is facilitated.

11 Claims, No Drawings

FIBROUS SURGICAL COMPRESS WITH COVER LAYER AUTOGENOUSLY BONDED TO ABSORPTION LAYER

This is a continuation of application Ser. No. 301,101 filed Sept. 17, 1981 abandoned.

BACKGROUND OF THE INVENTION

The invention relates to a surgical compress made from an absorptive layer and a liquid-permeable covering layer.

A similar compress is disclosed in German Petty Pat. No. 77 03 897. The cover layer is a non-woven fabric of polypropylene, polyethylene-polyester, and/or polyamide fibers which is interlocked in itself. Using hot calendering techniques, the cover layer is joined to the absorption layer, which results in a paper-like stiff feel. A surgical compress of this type therefore insufficiently conforms to the surface of a wound and the emerging wound secretion is not absorbed equally at all points of compress contact. In particular, highly viscous secretions lead very easily to clogging the surface of the compress, which can result in further degradation of the absorptivity.

It is therefore an object of the invention to develop a particularly soft and conformable surgical compress with a smooth surface which efficiently absorbs substantially all types of secretions occurring in the medical field.

SUMMARY OF THE INVENTION

According to the invention, there has been developed a surgical compress comprising an absorptive layer connected to a liquid permeable covering layer of hydrophobic, hydrolysis-resistant, aliphatic polyurethane fibers.

DETAILED DESCRIPTION OF THE INVENTION

The cover layer of the invention can be substantially wet with aqueous media so that wound secretions appearing on the surface are quickly conducted into the absorption layer. The cover layer itself absorbs no moisture or fluids and its good permeability for air and wound secretions is thereby fully preserved after extended use. The surface conformability and softness in connection with the foregoing properties make surgical compress particularly well suited for long-term dressings such as those necessary for the treatment of burn wounds.

The surgical compress shows no heat related effects up to temperatures of approximately 180° C. It can therefore be sterilized as usual at a temperature of about 130° C. and can be used accordingly.

In a particular embodiment, the cover layer has an area weight of from 10 to 50 g/m$^2$, and consists of fibers with a diameter of 15 to 40 microns. In this embodiment the cover layer is accordingly extremely thin and has a very coarse structure. Surprisingly, a surface nevertheless is obtained which is completely free from projecting naps of the absorption layer and wound adherence of the compress during the healing process is reliably prevented.

The polyurethane fibers of the covering layer are preferably bonded autogenously to each other in a non-woven fashion, i.e, without the addition of any foreign material which could result in a detrimental influence on the healing process. The fibers are related to each other in a random distribution, i.e., a preferred fiber orientation in any direction is not recognizable. The cross-section shape through the fibers is preferably circular. While it is possible to use fibers with a different cross-section, this can lead to a degradation of the permeability toward highly viscous secretions. Therefore, the use of fibers with a circular cross-section is preferred.

The polyurethane fibers may have finite length, for instance a length of 4 to 80 cm. Such fibers can be produced, using a spray-spinning technology, for example, by electrostatic spinning of a dissolved aliphatic polyurethane. If such a spinning process is used, micropores on the surfaces of the individual fibers are obtained in which, if desired, secondary substances for promotion of wound healing can be embedded.

In accordance with the present invention, the use of a cover layer is preferred which is composed of endless fibers as can be obtained through the use of the well-known extrusion-spinning technology. The surfaces of fibers produced in this manner are completely free of pores and smooth, whereby the embedding of wound secretion and thereby wound adherence of the compress, is prevented even more effectively. The prescribed circular cross-section and the diameter of the fibers as well as their mutual relation can be controlled very exactly and the production of such cover layers poses no problems. It is a further advantage that cover layers of this type contain no foreign materials which would have a detrimental effect on the healing process.

The cover layer and the absoprtion layer can be made in independent operations and can subsequently be joined together. Because of the extremely low area weight, the cover layer has very little dimensional and shape stability. Therefore, special measures have to be taken when making separate cover and absorption layers in order to ensure uniform lamination of the two layers. Such special measures include hot needle penetration lamination, pressure-heat lamination, needle punching, and other similar techniques.

According to the present invention, a preferred method of producing the two layers is one wherein the absorption layer is smoothed and the polyurethane fibers are spun directly thereon, the conditions of the process being adjusted so that the fibers bond to each other and to the absorption layer during the deposition and retain their identity.

The absorption layer can consist of the customary cellulose fibers, and it may have a layer thickness of, for example, 3 to 5 mm. It is smoothed in a heated calendar which consists of a steel and a cotton cylinder which are set against each other at a temperature of 140° C. with a line pressure of 35 kg/cm. The operating speed is 25 m/min. The absorption layer subsequently exhibits a high-quality, smooth surface. The fibers of the cover layer are spun onto the absorption layer at a distance of 10–20 cm. During their deposition, the fibers are still tacky, which results in a mutual bond to each other and to the absorption layer. In addition, a stabilization of the surface structure of the absorption layer is obtained, i.e., the surface smoothness produced in the preceding calendering operation is largely preserved after cooling-down. The surface of the cellulose layer is completely free of naps and protruding fiber ends. For ordinary applications, a further post-treatment is therefore not necessary. If the surgical compress is to be used in plastic surgery, it may be advantageous to let a further operation follow, such as a post-treatment in a calendar of the type discussed above, the cylinders of which are heated to a temperature of 80° C. with a line pressure of 20 kg/cm and an operating speed of 20 m/min.

We claim:

1. A fibrous surgical compress, which comprises: a fibrous absorption layer and an overlapping, liquid permeable, fibrous cover layer having a smooth outer surface which is free of protruding nap and fiber ends, the cover layer being autogeneously bonded to the absorption layer by direct formation of tacky cover layers fibers on the absorption layer, said tacky fibers thereafter drying to produce pressureless, interlayer autogeneous bonding and pressureless, random fashion, intralayer fiber autogeneous bonding; said fibers being comprised of hydrophobic, hydrolysis-resistant, aliphatic urethane fibers.

2. A surgical compress according to claim 1 wherein the outer surface of the cover layer is free of protruding nap and fiber ends of the absorption layer.

3. A surgical compress according to claim 1 wherein the surface of the absorption layer bonded to the cover layer is smooth and is free of protruding nap and fiber ends.

4. A surgical compress according to claim 1 wherein the surfaces of the polyurethane fibers are microporous.

5. A surgical compress according to claim 1 wherein the surfaces of the polyurethane fibers are smooth and free of pores.

6. A surgical compress according to claim 5 wherein the fibers are endless.

7. A surgical compress according to claim 1 wherein the polyurethane fibers have a length of about 4 to 80 cm.

8. A surgical compress according to claim 1 wherein the fibers have a circular cross-section.

9. A surgical compress according to claim 1 wherein the fibers are endless.

10. A method for manufacturing a surgical compress, said compress being described by claim 1, which comprises: smoothing the absorptive layer on calendar rollers and spinning the hydrophobic fibers of the covering layer directly onto the absorptive layer while the absorptive layer is warm, wherein the spinning and calendering conditions are adjusted so that the fibers are deposited on the warm absorptive layer while still tacky but retain their identity and bond to each other and to the absorptive layer without further heat or pressure.

11. A method according to claim 10 wherein the fibers are spun using an extrusion-spinning process.

* * * * *